United States Patent [19]
Webster

[11] Patent Number: 5,478,304
[45] Date of Patent: Dec. 26, 1995

[54] ANTI-STURRERING DEVICE AND METHOD

[76] Inventor: Ronald L. Webster, Hollins College, Roanoke, Va. 24020

[21] Appl. No.: 154,088

[22] Filed: Nov. 18, 1993

Related U.S. Application Data

[63] Continuation of Ser. No. 949,161, Sep. 23, 1992, abandoned.
[51] Int. Cl.⁶ ......................................................... A61F 5/58
[52] U.S. Cl. ................................................................ 600/23
[58] Field of Search ...................... 600/23–24; 128/715, 128/897–898, 746

[56] References Cited

U.S. PATENT DOCUMENTS

| | | | |
|---|---|---|---|
| 3,349,179 | 10/1967 | Klein | 600/23 |
| 3,566,858 | 3/1971 | Larson | 600/23 |
| 4,218,584 | 8/1980 | Attenburrow. | |
| 4,310,730 | 1/1982 | Aaroe | 179/110 A |
| 4,421,488 | 12/1983 | Parlenvi et al. | 434/185 |
| 4,685,448 | 8/1987 | Shames et al. | 600/23 |
| 4,784,115 | 11/1988 | Webster | 600/24 |

FOREIGN PATENT DOCUMENTS

| | | | |
|---|---|---|---|
| 2102171 | 1/1983 | United Kingdom | 600/23 |
| 2132089 | 7/1984 | United Kingdom | 600/23 |

*Primary Examiner*—Angela D. Sykes
*Attorney, Agent, or Firm*—Rogers & Killeen

[57] ABSTRACT

An anti-stuttering device and method for enhancing the fluency of speech in stutterers. The device consists of a microphone for detecting an individual speaker's tissue conducted vocal pulses ("voice") at the junction of the mandible and skull for transmission to the ear canal of the speaker where they are reproduced as audio signals. A predetermined delay, imperceptible to the speaker, is introduced into these non-tissue conducted voice related audio signals applied to the ear canal to thereby achieve a unique temporal relationship with respect to the arrival at the speaker's ear canal of tissue conducted audio signals related to that individual speaker's vocal pulses.

24 Claims, 2 Drawing Sheets

ANTI-STURRERING DEVICE AND METHOD

This is a continuation of application Ser. No. 949,161, filed Sep. 23, 1992, now abandoned.

BACKGROUND OF THE INVENTION

The present invention relates generally to a method and device for reducing stuttering and more particularly, to an anti-stuttering device and method for transmitting non-tissue conducted voice related signals to the speaker's ear to react with tissue transmitted voice related signals.

As indicated in the Webster U.S. Pat. No. 4,784,115 dated Nov. 15, 1988, the application of a non-tissue conducted audio signal related to the vocal pulses of a stutterer to a sealed ear canal has proven highly beneficial in therapy. It has now been discovered that the benefit may be a result of the interaction of tissue conducted and non-tissue conducted audio signals related to the vocal pulses of the speaker, and that the temporal relationship between the tissue conducted and non-tissue conducted acoustic signals may be selectively varied to maximize the benefit to a particular speaker.

As it is well known, there is a substantial difference between "voice" and "speech". "Voice" sounds are associated with the opening and closing of the vocal folds in the throat of the speaker and are low frequency signals generally less than 500 Hz in frequency, i.e., typically somewhat lower for males (125–150 Hz) than for females (225–300 Hz). These "vocal pulses" are sometimes referred to as the "vocal buzz" or "vocal tones". "Voice" is that background of tissue-conducted sound a speaker hears through his body (i.e., "tissue conducted") which others do not hear. This addition of "voice" to "speech" accounts for the difference in sound a person hears when speaking and when listening to his recorded speech.

"Speech" is generally understood to be the complex time varying signals recognized as possessing communication value and involves a conduction of sound through the air.

The application of a non-tissue conducted voice signal within a sealed ear canal of a speaker is described and claimed in said Webster patent, the disclosure of which is hereby incorporated herein by reference.

SUMMARY OF THE INVENTION

It is accordingly an object of the present invention to provide a novel anti-stuttering device and method for providing speech therapy.

It is another object of the present invention to provide a novel anti-stuttering device and method in which the sounds of the speaker's vocal pulses are detected and applied as non-tissue conducted sound to the ear canal of the speaker with a unique temporal relationship to the tissue conducted sounds of the vocal pulses.

It is another object of the present invention to provide an anti-stuttering device and method for providing speech therapy in which the relationship between tissue and non-tissue conducted signals may be selectively varied.

It is a further object of the present invention to provide a novel anti-stuttering device and method in which the vocal pulses are detected in proximity to the ear to thereby minimize both extraneous noise and the inconvenience of long cords, etc. to the wearer.

It is yet another object of the present invention to provide a novel anti-stuttering device and method in which the characteristics of the non-tissue conducted signal may be selectively varied.

It is yet a further object of the present invention to provide a novel anti-stuttering device and method in which the sounds of the vocal pulses are enhanced relative to other ambient noise for application to the wearer's ear.

It is yet still another object of the present invention to provide a novel microphone useful in voice detection for speech therapy.

These and other objects and advantages will be readily apparent to one skilled in the art to which the invention pertains from a perusal of the claims and the following detailed description of the preferred embodiment when read in conjunction with the appended drawings.

DETAILED DESCRIPTION OF THE PREFERRED EMBODIMENTS

Figure 1:
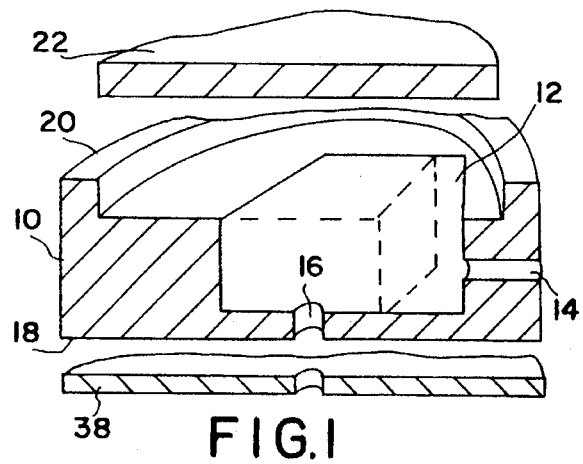
FIG. 1 is a pictorial representation, in vertical cross section, illustrating one embodiment of a housing for the device of the present invention.

With reference to FIG. 1, a housing 10 of any suitable conventional material, e.g., plastic, may be formed by molding or otherwise with a central cavity 12. The housing 10 may be generally disk-shaped and provided with a circumferential rim 20 to form seating for a disk 22 which forms the top or external surface of the housing 10. The cavity 12 may communicate by a passageway 14 to one lateral edge of the housing 10 and through a passageway 16 to the generally planer lower surface 18.

Figure 2:
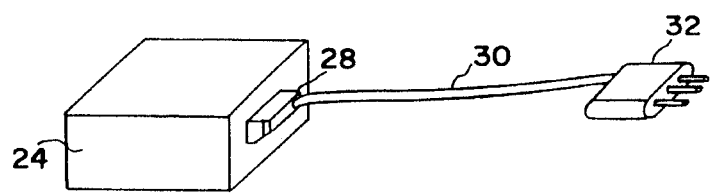
FIG. 2 is a pictorial representation of one embodiment of the novel transducer of the present invention.
Figure 3:
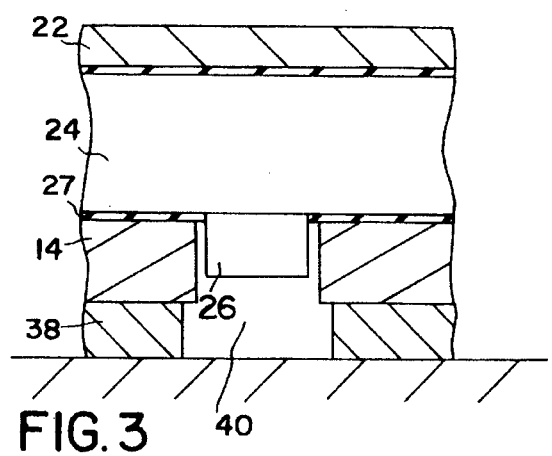
FIG. 3 is an elevation, in vertical cross section, of a portion of the housing of FIG. 1 with the transducer of FIG. 2 installed therein, which figure illustrates the method of mounting the housing to the skin and formation of the shielded air pocket.
Figure 4:
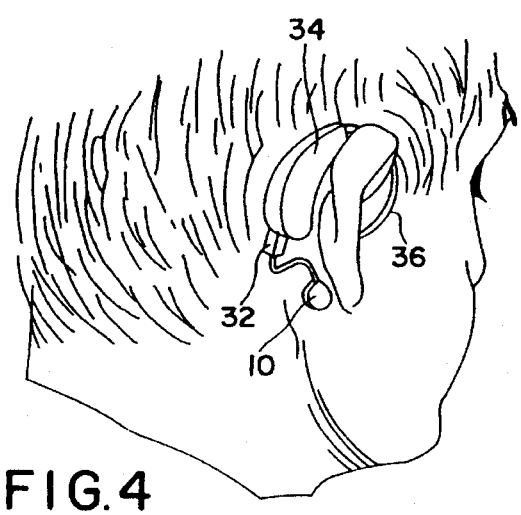
FIG. 4 is a pictorial view of the apparatus of the present invention as worn by a stutterer.

As shown in FIGS. 2 and 3, the transducer 24 may be in a suitable conventional transducer having a sensing element 26 depending therefrom. The housing is desirably shielded against ambient sounds by means of a lead foil 27 and may be provided with a connector 28 and conductor 30 to a suitable conventional plug 32 for connection to a conventional appropriate earpiece such as illustrated in FIG. 4 and in said Webster patent. The earpiece 34 may be provided with a suitable conventional deep ear probe 36 such as disclosed, for example, in said Webster patent.

With continued reference to FIGS. 1 and 2, the assembly of the transducer into the housing may be accomplished by the removal of a cover 22 from the housing to expose the cavity 12, the insertion of the plug 32 downwardly through the cavity 12 and out of the passageway 14 to thereby position the transducer 24 within the cavity 12 with the sensor 26 projecting into the passageway 16. The cover 22 may then be mated with the housing 10 to close the cavity 12.

As shown in FIGS. 1 and 3, the housing 10 may be attached to the wearer by means of a suitable conventional two-sided adhesive annulus 38 adapted to adhere both to the bottom of the housing 10 and to the skin of the wearer. By use of the removable adhesive annul! us 38, the housing 10 may be attached to the skin of the patient, desirably adjacent the junction of the mandible with the skull as illustrated in FIG. 4.

As indicated in FIG. 3, the passageway 16 and the central aperture of the adhesive 38 form an air pocket 40 to which sounds eliminating from the skin of the wearer are transmitted by air to the transducer 24.

This air pocket has been found to be of considerable value. The body produces many low frequency sounds, e.g., heartbeat, respiration, digestion, etc. These sounds appear to be of less amplitude than voice, and by virtue of the normal attenuation as they pass through the body, voice is more easily detected on the patient's head. The use of an air pocket further attenuates these signals and largely obviates the sounds of contact between microphone and hair or clothing as the patient moves.

As reported in "Manipulation Of Vocal Tone: Implications For Stuttering", Webster, *Speech Motor Control and Stuttering*, Elsevier Science Publishers, B. V., 1991, Ch. 51, the content of which is hereby incorporated herein by reference, the physiological aspects of the present invention are not fully understood. In general, the vocal pulses are transmitted to the ear canal of the speaker as tissue conducted audio signals. These vocal pulses are also detectable at various skin surfaces of the speaker and the junction of the mandible with a skull has been found particularly desirable. These vocal pulses may be detected by the transducer 24 by way of the air pocket 40 illustrated in FIG. 3, and may be amplified, shaped and/or otherwise processed in the earpiece 32 of FIG. 4. They may then be applied by the probe 36 to the ear cavity as a non-tissue conducted acoustic signal related to the vocal pulses. Thus, the auditory system receives both tissue conducted signal and a non-tissue conducted signal.

Figure 5:
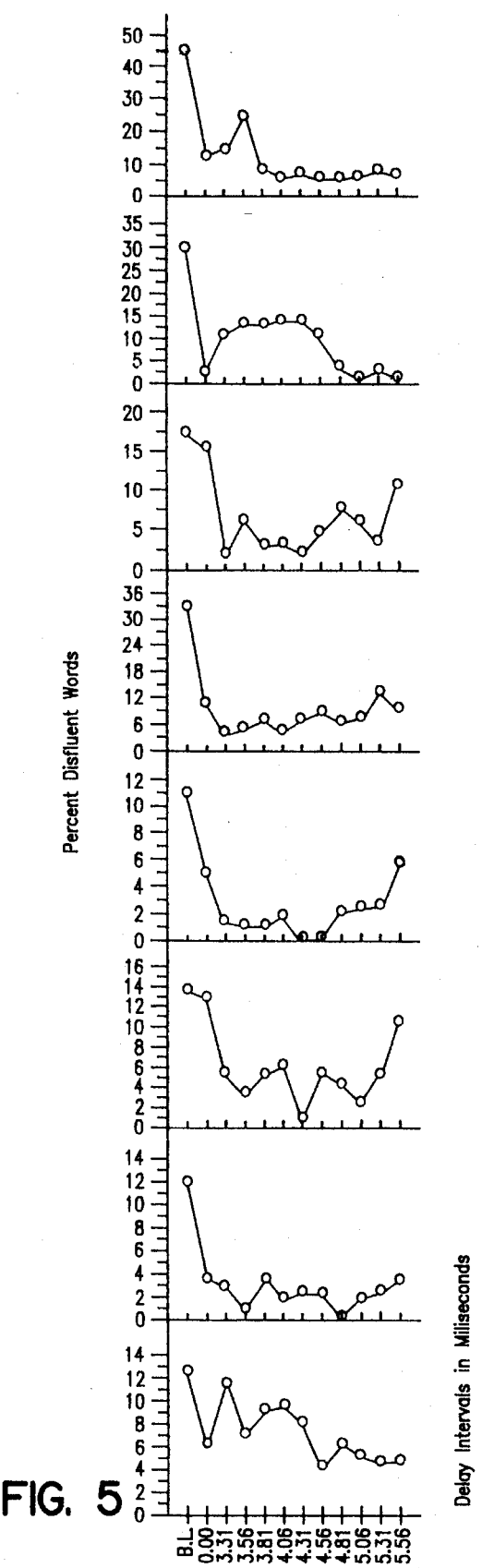
FIG. 5 is a graphical representation of the test results achieved from the test of eight patients illustrating the change in percent disfluent words as a function of the delay introduced in the non-tissue conducted signal to the ear canal.

These two signals are believed to be inherently out of phase as a result of the length of the conduction paths and the sound transmitting characteristics thereof. As illustrated in FIG. 5, there is generally a significant fluency enhancement without the use of any additional delay of the non-tissue conducted signal. However, and as illustrated in FIG. 5, the fluency enhancement varied from patient to patient significantly with the introduction of additional delay. For a particular patient, is desirable to measure the fluency enhancement with different increments of delay, and to thereafter select the delay which is most beneficial for that patient.

Figure 6:
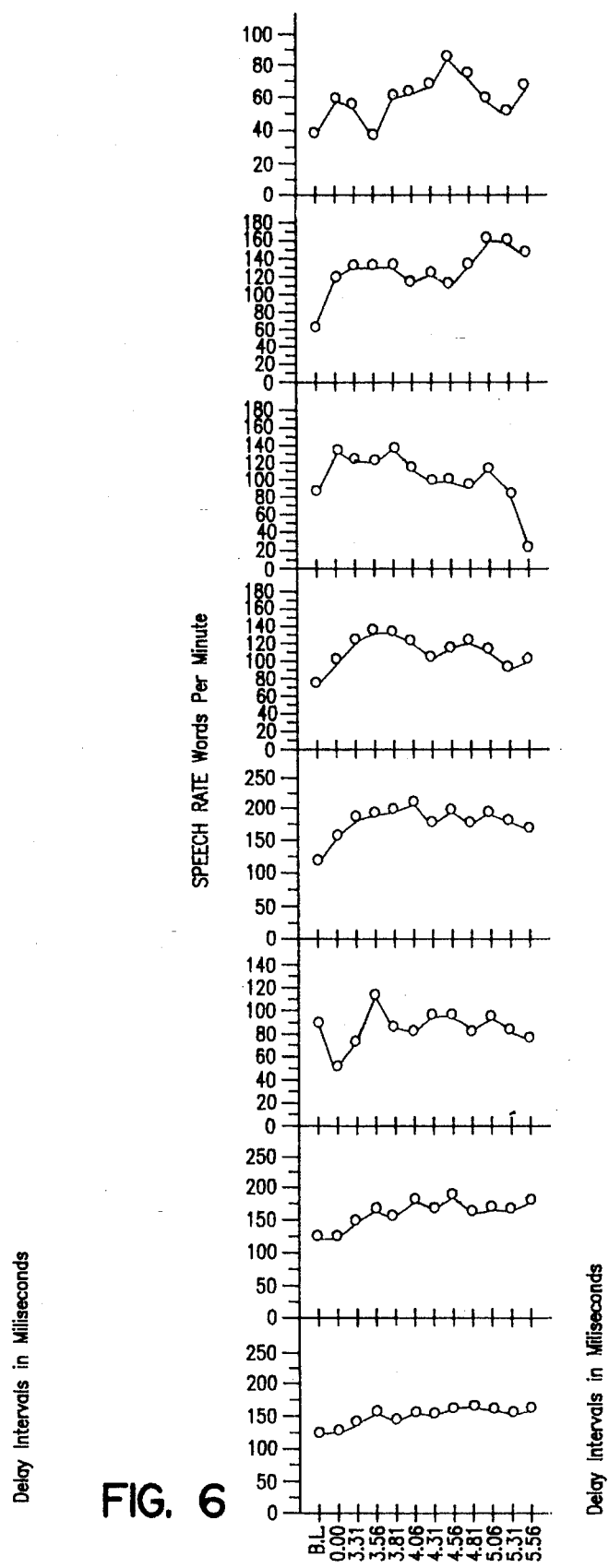
FIG. 6 is a graphical representation of the test results achieved from a test of the same eight patients of FIG. 4 illustrating the change in speech rate as a function of the delay in the application of the non-tissue conducted signal to the ear canal.

As shown in FIG. 6, the speech rate also varies significantly from patient to patient with continuing increases in the delay of the non-tissue conducted signal, the rate generally being highest at those delay intervals at which fluency was most enhanced.

Because of the different paths for the tissue related conducted signal to ears of the patient, and different physical characteristics, it may be desirable to apply the non-tissue conducted signal to both ears with differing incremental delays.

It appears to be important that the non-tissue conducted signal be related to the vocal pulses both as to its onset and duration, and it has been found desirable to isolate voice from other signals present in the body and in the environment in which the patient exists, including his own speech. To this end, it desirable to filter out and/or otherwise alternate sounds having a frequency above about 500 Hz, although this upper limit is desirably adjusted depending upon the vocal pulse characteristics of an individual patient. In addition, the use of the adhesive annulus to seal the housing to the skin of the patient and thereby define the air pocket helps to reduce ambient noise. Similarly, the use of a lead foil or other shielding for the transducer has been found to be helpful in attenuating external sounds including the patients own speech.

While the preferred embodiment of the present invention has been described, many variations and modifications will naturally occur to those skilled in the art from a perusal hereof. It is therefore to be understood that the embodiment described herein is illustrative only, and that the scope of the invention is one accorded a full range of equivalence.

What I claim is:

1. A method of speech therapy comprising the step of supplementing in a speaker's ear the tissue conducted sound related to the speaker's vocal pulses with non-tissue conducted sound related to the speaker's vocal pulses wherein the supplementing non-tissue conducted sound is selectively delayed relative to the tissue conducted sound.

2. The method of claim 1 wherein the step of supplementing includes applying the supplementing non-tissue conducted sound deep within the speaker's ear canal.

3. A method of speech therapy comprising the steps of:
   (a) applying sound related to the speaker's vocal pulses into the speaker's ear canal to supplement the sound of the vocal pulses that reaches the speaker's ear by way of tissue conduction; and
   (b) varying the phase relationship between non-tissue conducted and tissue conducted sound.

4. The method of claim 3 including deriving the non-tissue conducted sound from a microphone located adjacent the skin of the speaker in a location where the amplitude of tissue conducted sounds related to the speaker's vocal pulses is significantly greater than the amplitude of sounds related to the speaker's speech.

5. The method of claim 4 wherein the step of deriving includes locating the microphone adjacent the junction of the speaker's mandible and skull.

6. The method of claim 3 wherein the step of applying includes introducing the non-tissue conducted sound into the ear of the speaker by deep insertion tips.

7. The method of claim 3 wherein the steps of applying includes introducing the non-tissue conducted sound into both of the ears of the speaker.

8. A method of speech therapy comprising the steps of:
   (a) detecting tissue conducted sound related to a speaker's vocal pulses;
   (b) providing electrical signals related to the detected tissue conducted sound;
   (c) selectively delaying the electrical signals; and
   (d) transforming the electrical signals into sound within the speaker's ear canal to thereby enhance fluency.

9. The method of claim 8 wherein the step of detecting includes detecting the tissue conducted sound by a microphone located adjacent the skin of the speaker in proximity to the ear of the speaker.

10. The method of claim 9 wherein the step of detecting includes detecting the tissue conducted sound by a microphone located adjacent the skin of the speaker in a location where the amplitude of sounds related to the vocal pulses is significantly greater than the amplitude of sounds related to the speech of the speaker.

11. The method of claim 10 wherein the step of detecting includes detecting the tissue conducted sound by a microphone located adjacent the skin of the speaker and adjacent the junction of the mandible and skull.

12. The method of claim 10 wherein the step of providing electrical signals includes enhancing the amplitude of the electrical signals having a frequency less than about 500 Hertz relative to the amplitude of the electrical signals having a frequency greater than about 500 Hertz.

13. The method of claim 12 wherein the enhancement includes the step of filtering out undesired frequency components.

14. The method of claim 12 wherein the enhancement includes the step of amplifying desired frequency components.

15. The method of claim 8 wherein the step of transforming includes introducing non-tissue conducted sound into the ear of the speaker by deep insertion tips.

16. The method of claim 8 wherein the step of transforming includes introducing non-tissue conducted sound into both of the ears of the speaker.

17. The method of claim 16 wherein the step of delaying includes providing a delay in the insertion of the non-tissue conducted sound which is different for each ear of the speaker.

18. The method of claim 8 wherein the step of transforming includes selectively varying the shape of the electrical signals.

19. The method of claim 8 wherein the step of detecting includes detecting the tissue conducted sound by a sensor which is lead shielded to reduce the detection of non-tissue conducted sounds.

20. An electronic hearing aid comprising:
   means for detecting tissue conducted sounds related to the vocal pulses of the wearer; and
   means responsive to said detection means for providing an audio signal deep within the ear cavity of the wearer, said signal having a predetermined time delay relative to the detected tissue conducted sounds.

21. The hearing aid of claim 20 including means for shielding said detection means from non-tissue conducted sounds.

22. The hearing aid of claim 20 wherein said detecting means is configured to detect tissue conducted sounds adjacent the mandible/skull junction of the wearer.

23. A method of speech therapy comprising the steps of:
   (a) placing a first transducer for converting tissue conducted vocal pulse sounds to electrical signals adjacent the skin of a speaker in proximity to the ear of the speaker near the junction of the mandible and the skull;
   (b) spacing the first transducer from the skin of the speaker so that the vocal pulse sounds are conveyed from the skin of the speaker to the first transducer through a column of air that is protected from non-tissue conducted sounds, whereby low frequency body-produced sounds are attenuated by the column of air;
   (c) providing the electrical signals from the first transducer to a second transducer within the speaker's ear canal, the second transducer converting the electrical signals to near-replicas of the vocal pulse sounds;
   (d) spacing the second transducer from the skin of the ear canal of the speaker so that the near-replicate sounds are conveyed from the second, transducer to the skin of the ear canal of the speaker through a column of air that is protected from non-tissue conducted sounds, whereby low frequency body-produced sounds are attenuated by the column of air; and
   (e) supplementing in the speaker's ear canal the tissue conducted sound related to vocal pulses received in the ear canal with the near-replicate sound from the second transducer.

24. The method of claim 23 further comprising the step of selectively delaying the near-replicate sound from the second transducer relative to the tissue conducted sound related to vocal pulses received in the ear canal.

* * * * *

UNITED STATES PATENT AND TRADEMARK OFFICE
CERTIFICATE OF CORRECTION

PATENT NO. : 5,478,304
DATED : December 26, 1995
INVENTOR(S) : Ronald L. Webster It is certified that error appears in the above-indentified patent and that said Letters Patent is hereby corrected as shown below:

On the title page, item [54] title to read:

ANTI-STUTTERING DEVICE AND METHOD

Signed and Sealed this

Second Day of April, 1996

Attest:

BRUCE LEHMAN

*Attesting Officer*     *Commissioner of Patents and Trademarks*